United States Patent [19]
Bolish, Jr. et al.

[11] Patent Number: 4,902,499
[45] Date of Patent: * Feb. 20, 1990

[54] HAIR CARE COMPOSITIONS CONTAINING A RIGID SILICONE POLYMER

[75] Inventors: Raymond E. Bolich, Jr., Maineville; Daniel S. Cobb, Loveland, both of Ohio; Vincent J. Kwasniewski, Minneapolis, Minn.; Michael A. Snyder, Fairfield; David M. Stentz, Cincinnati, both of Ohio

[73] Assignee: The Procter & Gamble Company, Cincinnati, Ohio

[*] Notice: The portion of the term of this patent subsequent to Aug. 16, 2005 has been disclaimed.

[21] Appl. No.: 31,480

[22] Filed: Mar. 27, 1987

Related U.S. Application Data

[63] Continuation-in-part of Ser. No. 848,414, Apr. 4, 1986.

[51] Int. Cl.$^4$ ............... A61K 7/075; A61K 7/08; A61K 7/11
[52] U.S. Cl. ......................... 424/70; 424/71; 424/DIG. 2; 424/47; 252/DIG. 13
[58] Field of Search ................ 424/70, 71; 252/DIG. 13, 555

[56] References Cited

U.S. PATENT DOCUMENTS

| | | | |
|---|---|---|---|
| 3,957,970 | 5/1976 | Korkis | 424/70 |
| 3,964,500 | 6/1976 | Drakoff | 132/7 |
| 4,185,087 | 1/1980 | Morlino | 424/70 |
| 4,221,688 | 9/1980 | Johnson et al. | 524/251 |
| 4,344,763 | 8/1982 | Tolgyesi et al. | 8/127.51 |
| 4,364,837 | 12/1982 | Pader | 252/173 |
| 4,387,090 | 6/1983 | Bolich | 424/70 |
| 4,450,152 | 5/1984 | Ona et al. | 424/70 |
| 4,472,375 | 9/1984 | Bolich, Jr. et al. | 424/70 |
| 4,487,883 | 12/1984 | Homan | 524/792 |
| 4,502,889 | 3/1985 | Kurita | 106/287.12 |
| 4,515,784 | 5/1985 | Bogardus et al. | 514/63 |
| 4,529,586 | 7/1985 | DeMarco et al. | 424/70 |
| 4,704,272 | 11/1987 | Oh et al. | 424/70 |
| 4,728,457 | 3/1988 | Fieler et al. | 252/DIG. 13 X |
| 4,741,855 | 5/1988 | Grote et al. | 424/70 X |
| 4,764,363 | 8/1988 | Bolich, Jr. | 424/47 |

OTHER PUBLICATIONS

Chemical Abstracts, vol. 94, No. 2, May 1981, p. 373, col. 1, Abstract No. 162601q.
Chemical Abstracts, vol. 97, No. 23, Dec. 1982, p. 324, col. 1, Abstract No. 203098p.

*Primary Examiner*—Ellis P. Robinson
*Assistant Examiner*—Susan S. Rucker
*Attorney, Agent, or Firm*—Douglas C. Mohl; Steven J. Goldstein; Gretchen R. Hatfield

[57] ABSTRACT

Hair care compositions which give both improved style retention and hair conditioning properties. The compositions comprise from about 0.01% to about 10% of a rigid silicone polymer and a volatile carrier.

35 Claims, No Drawings

HAIR CARE COMPOSITIONS CONTAINING A RIGID SILICONE POLYMER

CROSS REFERENCE TO RELATED APPLICATION

This is a continuation-in-part application of our co-pending application having Ser. No. 848,414, filed Apr. 4, 1986.

TECHNICAL FIELD

The present invention relates to hair care compositions which have improved hair conditioning and style retention properties due to the inclusion of particular types of silicone polymers, and a volatile carrier for such polymers.

BACKGROUND OF THE INVENTION

The desire to have hair retain a particular shape is widely held. The two methodologies of accomplishing this are permanent chemical alteration of the hair or a temporary alteration. A temporary alteration is one which can be removed by water or by shampooing. This has generally been accomplished by means of the application of a separate composition to dampened hair, i.e., after shampooing and/or conditioning, and prior to drying and/or styling. The materials used to provide setting benefits have generally been resins or gums and have been applied in the form of mousses, gels, lotions, and sprays. However, many people desire some improvement in style retention without the necessity of a separate step. Further, some people desire a high level of style retention such as that provided by a separate composition without the negative impact of these materials on dry hair properties, particularly ease of combing and hair feel.

Silicones in various hair care compositions have been disclosed in a large number of different publications, including U.S. Pat. No. 3,964,500, Drakoff, issued June 22, 1976; U.S. Pat. No. 4,364,837, Pader, issued Dec. 21, 1981; U.S. Pat. No. 4,341,799, Good, issued July 27, 1982; U.S. Pat. No. 4,465,619, Boskamp, issued Aug. 14, 1984; U.S. Pat. No. 4,515,784, Bogartus, issued May 7, 1985; U.S. Pat. No. 4,387,090, Bolich, issued June 7, 1983; and U.S. Pat. No. 4,529,586, DeMarco et al, issued July 16, 1985.

It has now been discovered that hair care compositions comprising certain rigid silicone polymers and volatile carriers provide increased style retention. The compositions may be in any of the conventional forms, including but not limited to shampoos, conditioners, hairsprays, tonics, lotions and mousses. The compositions provide the increased style retention to the hair without decreasing dry hair properties such as ease of combing.

This is surprising since other silicone materials which have been typically used in hair care compositions as conditioners have hurt style retention, and the resins and gums used frequently for style retention have generally hurt dry hair properties such as combing.

It is an object of the present invention to provide hair care compositions which contain a high molecular weight rigid silicone polymer.

It is a further object of the present invention to provide stable hair care compositions containing a volatile carrier.

It is a further object of the present invention to provide hair care compositions providing good style retention.

It is a further object of the present invention to provide hair care compositions which provide good conditioning.

It is a further object of the present invention to provide an improved method of temporarily styling and conditioning hair.

It is a further object of the present invention to provide a method of treating hair for improved style retention.

These and other objects will become readily apparent from the detailed description which follows.

Unless otherwise indicated, all percentages and ratios herein are by weight.

SUMMARY OF THE INVENTION

The present invention relates to hair care compositions comprising from about 0.01% to about 10% of a rigid silicone polymer, from about 0.1% to about 99.9% of a volatile carrier or mixtures thereof.

DETAILED DESCRIPTION OF THE INVENTION

The essential as well as optional components are described below.

Rigid Silicone Polymer

The compositions of the present invention contain at least one rigid silicone polymer which when applied to hair imparts style retention benefits.

The polymers comprise from about 0.01% to about 10% of the composition, preferably from about 0.05% to about 7%.

Polymers useful in the present invention include, but are not limited to, filler reinforced polydimethyl siloxane gums including those having end groups such as hydroxyl, cross linked siloxanes such as organic substituted silicone elastomers, organic substituted siloxane gums including those having end groups such as hydroxyl, resin reinforced siloxanes and cross linked siloxane polymers.

The rigid silicone polymers useful in the present invention have complex viscosities of at least $2 \times 10^5$ poise (P), preferably about $1 \times 10^7$ or more, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum is a diphenyl-dimethyl polysiloxane gum useful in the invention has a molecular weight of at least about 500,000, and must be diphenyl substituted to the extent of 3% or more, preferably at least about 5%.

The siloxane gums may be filler reinforced to provide additional rigidity. Silica is the preferred filler.

The silicone elastomer useful in the compositions of the present invention is that type of material described in U.S. Pat. No. 4,221,688, Sept. 9, 1980 to Johnson et al, incorporated herein by reference. The actual material described in the patent and what is put into the present compositions is an aqueous emulsion which dries to form an elastomer upon removal of the water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to about 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of a diorganotindicarboxylate (e.g., dioctyl tindilaurate) catalyst is from 0.1 to 2 parts. The elastomer emulsion is used in an amount of from about 0.1% to about 5%, preferably from about 0.5% to about 4% of the total composition.

Silicone resins are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use.

Other rigid silicone polymers of interest are those siloxanes which have been sparingly crosslinked but are still soluble in solvents such as cyclomethicone. Precursors for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur and high-energy radiation.

Volatile Carrier

The compositions of the invention comprise a volatile carrier, or mixtures thereof, which preferably is present from about 0.1% to about 99.9% for the silicone polymer. The term "volatile" as used herein means that the material has a measurable vapor pressure.

Where the rigid silicone polymer is a polydimethyl siloxane or a polydiphenyldimethyl siloxane, the preferred carriers are volatile silicones having a boiling point between 99° C. to about 260° C. and have a solubility in water of less than about 0.1%. The degree of substitution on the siloxane (higher substitution, lower solubility) obviously affects the polymer's solubility and is taken into account by the formulator. The silicones may be either cyclic or linear polydimethyl siloxanes. The number of silicon atoms in the cyclic silicones is about 3 to about 7, most preferably 4 or 5. The general formula for the cyclic silicones is:

[Si-O]$_n$

wherein n=3-7. Viscosities are generally less than 10 centipoise (cP) at 25° C.

Linear polydimethyl siloxanes useful in the invention generally have viscosities of less than about 5 cP at 25° C. The linear volatile silicones contain from about 3 to about 9 silicone atoms and have the general formula (CH$_3$)$_3$Si-O-[Si(CH$_3$)$_2$O]$_n$Si(CH$_3$)$_3$ wherein n=1-7.

Silicones of the above described types are widely available e.g., from Dow Corning as 344,345 and 200 fluids; Union Carbide as Silicone 7202 and 7158, and Stauffer Chemical as SWS-03314.

Also useful in compositions of the invention are certain volatile hydrocarbons. These hydrocarbons may be either straight chain or branched, and contain from about 10 to about 16 carbon atoms, preferably from about 12 to about 16 carbon atoms.

Water is also useful in compositions of the present invention either alone or in mixtures with other volatile carriers. Where the elastomer alone is used, water may be preferred and if so, a surfactant, as described below, is also present.

Short chain alcohols such as ethanol are also suitable solvents for use in the present compositions.

Optional Ingredients

Surfactants

Surfactants are preferred optional ingredients in the compositions of the invention, particularly shampoo and conditioner compositions. When present, the surfactant comprises from about 0.05% to about 50%. For a shampoo, the level is preferably from about 10% to about 30%, most preferably from about 12% to about 25% of the composition. For conditioners the preferred level of surfactant is from about 0.2% to about 3%. Surfactants useful in compositions of the invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae ROSO$_3$M and RO(C$_2$H$_4$O)$_x$SO$_3$M wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C$_{12-13}$ compounds; from 60 to 100% by weight of C$_{14-15-16}$ compounds, from about 0 to 20% by weight of C$_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the β-alkyloxy alkane sulfonates. These compounds have the following formula:

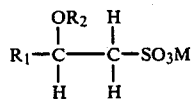

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include:

potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium β-n-propoxydodecylsulfonate.

Many additional nonsoap synthetic anionic surfactants are described in McCUTCHEON'S, DETERGENTS AND EMULSIFIERS, 1984 ANNUAL, published by Allured Publishing Corporation, which is incorporated herein by reference. Also U.S. Pat. No. 3,929,678, to Laughlin et al., issued December 30, 1975 discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

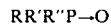

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactant vehicle materials among those useful herein are disclosed in the following documents, all incorporated by reference herein: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued June 7, 1983.

Among the quaternary ammonium-containing cationic surfacant materials useful herein are those of the general formula:

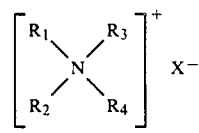

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups.

Other quaternary ammonium salts useful herein are of the formula:

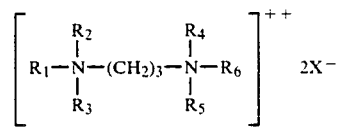

wherein $R_1$ is an aliphatic group having from 16 to 22 carbon atoms, $R_2$, $R_3$, $R_4$, $R_5$ and $R_6$ are selected from hydrogen and alkyl having from 1 to 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein in the alkyl groups have from 12 to 22 carbon atoms and are derived from long-chain fatty acids, such as hydrogenated tallow fatty acid. (Tallow fatty acids give rise to quaternary compounds wherein $R_1$ and $R_2$ have predominately from 16 to 18 carbon atoms.) Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(-hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant vehicle materials. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E. O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate and N-tallowpropane diamine dichloride and stearamidopropyl dimethylamine citrate. Cationic amine surfactants included among those useful in the present invention are disclosed in U.S. Pat. No. 4,275,055, Nachtigal, et al., issued June 23, 1981 (incorporated by reference herein).

Zwitterionic surfactants, useful in shampoos as well as conditioners, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

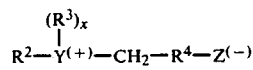

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, the ethoxylated alkyl sulfates and mixtures thereof are preferred for use herein.

Where the hair care compositions are conditioner compositions, preferred optional components include gel vehicle materials. The vehicle comprises two essential components: a lipid vehicle material and a cationic surfactant vehicle material. Such gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000—Cetostearyl Alcohol, I. Self Bodying Action", 38 *J. of Colloid and Interface Science* 616–625 (1972).

Lipid vehicle material:

The vehicles incorporate one or more lipid materials, (herein referred to as comprising a "lipid vehicle material", singly or in combination) which are essentially water-insoluble, and contain hydrophobic and hydrophilic moeities. Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3d edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification No. 1,532,585, published Nov. 15, 1978; and Fukushima, et al., "The Effect of Cetostearyl Alcohol in Cosmetic Emulsions", 98 *Cosmetics & Toiletries* 89–102 (1983). Fatty esters included among those useful herein are disclosed in U.S. Pat. No. 3,341,465, Kaufman, et al., issued Sept. 12, 1967 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Other vehicles, suitable for use with the rigid silicones herein are, for example, tonics, mousses and hairsprays. Tonics utilize a solvent such as water or alcohol while mousses and hairsprays additionally utilize a propellant such as trichlorofluoromethane, dichlorodifluoromethane, dimethylether, propane, n-butane or isobutane in addition to the rigid silicone and optional components as set forth below. The level of propellant can be adjusted as desired but is generally from about 3% to about 30% for mousses and from about 15% to about 40% for hairsprays.

The hair care compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; thickeners and viscosity modifiers such as a diethanolamide of a long chain fatty acid (e.g., PEG 3 lauric diethanolamide), cocomonoethanol amide, dimethicone copolyols, guar gum, methyl cellulose starches and starch derivatives, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts, hair reducing agents such as the thioglycolates; perfumes; and, sequestering agents such as disodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3 to about 10.

As with all compositions, the present compositions should not contain components which unduly interfere with the performance of the compositions.

METHOD OF MANUFACTURE

Methods of manufacture of various types of hair care compositions are described in the following examples.

INDUSTRIAL APPLICABILITY

The present compositions are used in a conventional manner varying with the type of composition described.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLE 1

Shampoo Compositions

| Component | Weight % | | | |
|---|---|---|---|---|
| Ammonium lauryl sulfate | 8.59 | | | |
| EDTA | 0.20 | | | |
| Citric acid | 0.79 | | | |
| Sodium hydroxide | 0.75 | | | |
| Cocamide MEA | 1.00 | | | |
| Glycol distearate | 1.50 | | | |
| Ammonium laureth-3 sulfate | 12.09 | | | |
| Cetearyl alcohol | 0.10 | | | |
| Silicone premix (see examples)[1] | | | | |
| Preservative | 0.03 | | | |
| Fragrance | 0.30 | | | |
| Distilled Water | q.s. | | | |

[1]Level of silicone premix varies with selection

| Silicone Premixes | I | II | III | IV |
|---|---|---|---|---|
| D-5 cyclomethicone | 1.50 | — | 1.50 | 1.50 |
| Polydimethyl siloxane[1] | 1.50 | — | 0.30 | — |
| Silica[2] | 0.26 | — | — | — |
| Silicone elastomer[3] | — | 3.00 | — | — |
| Purified resin[4] | — | — | 0.60 | — |
| Diphenyldimethyl siloxane | | | | |

-continued

| | | | | |
|---|---|---|---|---|
| gum[5] | — | — | — | 1.50 |

[1]SE-76 gum, supplied by General Electric Company
[2]Cab-O-Sil HS-5, supplied by Cabot Corporation
[3]Silicone elastomer Q3-5205, supplied by Dow Corning Corporation
[4]SR-545 resin, supplied by General Electric Company
[5]SE54 gum supplied by General Electric Company I. The polydimethyl siloxane and silica are intimately mixed in a high shear ribbon mixer for at least 2 hours. The blend is then dissolved in the D-5 cyclomethicone to form the silicone premix.
II. The silicone elastomer is added directly to the batch.
III. The resin is received as a solution in toluene. The toluene is stripped completely, and the purified resin is dissolved with the polydimethylsiloxane in the cyclomethicone.

Ammonium lauryl sulfate, EDTA, citric acid, and sodium hydroxide are added to the distilled water at about 15° C. The mixture is heated to from 70° C. to 80° C. The cocamide MEA and glycol distearate are added at this point. The ammonium laureth-3 sulfate, cetearyl alcohol and silicone premix are blended at from 70° C. to 90° C. This mixture is added to the batch following the glycol distearate. The preservative is then added. The batch is mixed for 5 minutes then cooled to room temperature (15° C. to 25° C.). The fragrance is added, then the batch is milled under high shear for at least 5 minutes using conventional milling apparatus.

EXAMPLE 2

Mousse Compositions

The following composition was prepared:

| Component | Weight % |
|---|---|
| Luvisokol ® VA55E (50% active)[1] | 9.00 |
| Propylene glycol | 2.00 |
| Carbopol ® 934[2] | 0.20 |
| Cocodimethyl amine oxide | 0.25 |
| Aminomethyl propanol | 0.30 |
| Glydant ®[3] | 0.37 |
| Perfume | 0.10 |
| D. C. Q3-5025 silicone elastomer (40% active)[4] | 2.50 |
| A-46 propellant[5] | 10.00 |
| Double reverse osmosis water | q.s. 100% |

[1]PVP/PVA Copolymer offered by BASF
[2]Carboxyvinyl polymer offered by B.F. Goodrich Co.
[3]Preservative offered by Glyco Chemical Co.
[4]Silicone elastomer offered by Dow Corning
[5]A mixture of propane (20%), isobutane (78%) and η-butane (2%) offered by Phillips Petroleum Company The aerosol mousses of the present invention are prepared by combining all ingredients except the aerosol propellant into a batch called the concentrate. This concentrate is made by slurrying the Carbopol with agitation in the water for several minutes until there are no Carbopol lumps. To this is added the aminomethyl propanol while increasing the agitator speed to accommodate the increase in viscosity accompanying neutralization. Maintaining vigorous agitation, the remaining ingredients except for Glydant and silicone elastomer are added and mixed until well dispersed. The Glydant and silicone elastomer are finally added and mixing continued until these are thoroughly dispersed. The resulting concentrate is very thick with a pH of 8.2. Aerosol mousse cans are prepared by placing 135 grams of concentrate into 5 oz. aluminum monobloc (epoxy lining) cans, placing mousse valves on can tops, drawing a vacuum to evacuate can headspace (to remove air), and crimping the valves into place. The propellant (15 grams) is added by pressure filling through the valve stem.

EXAMPLE 3

This is another example of a composition which was prepared.

| Component | Weight % |
|---|---|
| Luviskol K-30[1] (30% active) | 2.00 |
| Xanthan gum | 0.70 |
| Glydant | 0.37 |
| Nonoxynol-14 | 1.00 |
| D.C. Q3-5024 silicone elastomer (40% active)[2] | 1.00 |
| A-70 propellant[3] | 5.00 |
| Double reverse osmosis water | q.s. 100% |

[1]PVP polymer offered by BASF
[2]Silicone elastomer offered by Dow Corning
[3]A mixture of propane and isobutane offered by Phillips Petroleum Company

EXAMPLE 4

The following is another mousse composition representative of the present invention

| Component | Weight % |
|---|---|
| Gantrez ® ES 225[1] (50% active) | 4.00 |
| Carbopol 941 | 0.20 |
| Aminomethyl propanol | 0.80 |
| Glydant | 0.37 |
| A-46 | 8.00 |
| D.C. Q3-5024 silicone elastomer (40% active) | .50 |
| Double reverse osmosis H$_2$O | q.s. 100% |

[1]Copolymer of methylvinyl ether/maleic anhydride offered by GAF

EXAMPLE 5

Conditioner Compositions

A hair conditioner, according to the present invention, was made comprising:

| Component | Weight % |
|---|---|
| Hydroxyethyl cellulose | 0.50 |
| Quaternium-18[1] | 0.85 |
| Dimethicone copolyol[2] | 0.10 |
| Cetyl alcohol | 1.00 |
| Stearyl alcohol | 0.75 |
| Ceteareth-20 | 0.35 |
| Stearamidopropyl dimethylamine[3] | 0.50 |
| Glyceryl monostearate | 0.25 |
| Citric acid | 0.13 |
| Fragrance | 0.20 |
| Preservative | 0.03 |
| Rigid silicone premix[4] (see examples) | — |
| Distilled water | q.s. 100% |

[1]Adogen 442-100P, Sherex Chemical Company
[2]Dow Corning 190 Silicone Surfactant
[3]Lexamine S-13) Inolex Corporation
[4]Amount varies with type of premix selected Rigid Silicone Premix Examples

| Component | Weight % (total batch) |
|---|---|
| Polydimethylsiloxane[1] | 0.30 |
| Silica[2] | 0.05 |
| D-5 cyclomethicone | 1.70 |

[1]SE-76 gum, General Electric Company
[2]Cab-O-Sil HS-5, Cabot Corporation

The polydimethyl siloxane and silica are intimately mixed for at least 4 hours in a high shear ribbon mixer.

The resulting blend is dissolved in the cyclomethicone to form the premix used in the base formula.

| Component | Weight % (total batch) |
|---|---|
| Polydiphenyldimethyl siloxane[1] | 0.30 |
| D-5 cyclomethicone | 1.70 |

[1] SE-54 gum, General Electric Company

The polydiphenyl dimethyl siloxane is dissolved in the cyclomethicone to form the premix used in the base formula.

In place of the gum shown a resin reinforced gum may be used to form another premix.

Hydroxyethyl cellulose is added to the distilled water at a temperature of 15° C. to 40° C. This mixture is well dispersed, then heated to a temperature of from 60° C. to 90° C. Materials 2 through 8 are added to the batch while the temperature is maintained in this range. The mixture is stirred for approximately 10 minutes, then cooled to approximately 50° C. The remaining materials are added at this temperature. The mixture is milled under high shear for approximately 2 minutes using a conventional milling apparatus, then cooled to room temperature and collected.

EXAMPLE 6

A conditioner composition according to the present invention, is as follows:

| Component | Weight % |
|---|---|
| Hydroxyethyl cellulose | 0.50 |
| Quaternium-18 | 0.40 |
| Dimethicone copolyol | 0.10 |
| Cetyl alcohol | 1.00 |
| Stearyl alcohol | 0.75 |
| Ceteareth-20 | 0.35 |
| Stearamidopropyl dimethylamine | 0.50 |
| Glyceryl monostearate | 0.25 |
| Citric acid | 0.13 |
| Fragrance | 0.20 |
| Preservative | 0.03 |
| Silicone elastomer[1] | 1.00 |
| Double reverse osmosis water | q.s. 100% |

[1] Silicone Elastomer Q3-5205, Dow Corning Corporation A hair conditioning product, as comprised above, was made in a manner similar to that described in the base formula. This product, when applied to human hair, is useful as a hair conditioner. The silicone elastomer is added directly to the base formula.

EXAMPLE 7

An aerosol hairspray composition of the present invention is as follows:

| Component | Weight % |
|---|---|
| A-31 Propellant[1] | 75.00 |
| SDA40 200 proof ethanol | 22.00 |
| Silicone premix | 3.00 |
| Silicone Premix | Parts |
| Polydimethyl siloxane[2] | 2.50 |
| Silica[3] | .50 |

[1] Isobutane offered by Phillips Petroleum Company
[2] SE-76 gum, supplied by General Electric Company
[3] Cab-O-Sil HS-5, Cabot Corporation The polydimethyl siloxane and silica are intimately mixed in a high shear ribbon mixer for at least 4 hours. Aerosol hairspray cans are then prepared by adding 3 grams of silicone premix and 22 grams SDA40 200 proof ethanol to the aerosol can, placing valves on can tops, drawing a vacuum to evacuate can headspace (to remove air), and crimping valves into place. The propellant (75 grams) is added by pressure filling through the valve stem.

A premix containing 1% of the siloxane gum and 2% of purified resin SR545 may be used in place of the above-described premix.

EXAMPLE 8

The following is a pump spray tonic composition of the present invention:

| Component | Weight % |
|---|---|
| DIC Q3-5025 silicone Elastomer (40% active) | 4.00 |
| Sodium lauryl sulfate | 0.20 |
| Glydant | 0.37 |
| Perfume | 0.01 |
| Double reverse osmosis water | q.s. to 100% |

The ingredients are added in the order, water, sodium lauryl sulfate, perfume, Glydant, and silicone elastomer. The batch is mixed at ambient temperature for 20 minutes. The batch is then placed in pump bottle.

EXAMPLE 9

The following is a styling composition of the present invention:

| Component | Weight % |
|---|---|
| SDA 40 ethanol | 40.00 |
| Cyclomethicone (D5) | 2.00 |
| Silicone gum[1] | .05 |
| Benzoyl peroxide | .00005 |
| Fragrance | .05 |
| Double reverse osmosis water | q.s. 100% |

The silicone premix is prepared by first crosslinking the silicone gum with benzoyl peroxide. This is accomplished by thoroughly blending the benzoyl peroxide into the silicone gum with a ribbon or other suitable mixer. This mixture is then heated to about 150° C. for twenty minutes. The result crosslinked gum is then mixed with the cyclomethicone for several hours until it has fully dispersed.

The tonic itself is prepared by simply adding the premix to the water, fragrance, and ethanol. [1]: SE76 offered by General Electric

EXAMPLE 10

The following is another hair tonic composition of the present invention:

| Component | Weight % |
|---|---|
| Ethanol (SDA 40) | 40.0 |
| D-4 cyclomethicone | 1.56 |
| Dimethicone gum[1] | 0.013 |
| Silica[2] | 0.0024 |
| Fragrance | 0.20 |
| Water | q.s. 100% |

[1] SE-76 from General Electric
[2] Cab-O-Sil HS-5 from Cabot

The silica and dimethicone gum are intimately mixed for at least 2 hours in a high shear ribbon mixer. This compound is then dissolved in the cyclomethicone. This blend is added to the rest of the tonic formula.

EXAMPLE 11

The following is another hair tonic composition of the present invention:

| Component | Weight % |
| --- | --- |
| Ethanol (SDA 40) | 40.0 |
| D-5 cyclomethicone | 2.0 |
| Polydiphenyldimethyl siloxane[1] | 0.05 |
| Fragrance | 0.20 |
| Water | q.s. 100% |

[1]SE-54, General Electric

The polydiphenyl dimethyl siloxane is dissolved in the cyclomethicone. This blend is added to the rest of the tonic formula.

EXAMPLE 12

The following is yet another hair tonic composition of the present invention:

| Component | Weight % |
| --- | --- |
| Fragrance | 0.2 |
| Ethanol (SDA 40) | 30.0 |
| D-5 cyclomethicone | 1.5 |
| Dimethicone gum[1] | 0.187 |
| Purified resin SR545[2] | 0.375 |
| Water | q.s. 100% |

[1]SE-76, General Electric
[2]The resin is received as a solution in toluene from General Electric. The toluene is stripped completely, and the purified resin is dissolved at 50% in cyclomethicone. The dimethicone is also dissolved in a separate solution with cyclomethicone. The two solutions are blended together. This mixture is added to the rest of the formula.

What is claimed is:

1. A hair care composition comprising:
   (a) from about 0.01% to about 10% of a rigid silicone polymer having a complex viscosity of at least $1 \times 10^7$ poise, and
   (b) a volatile carrier wherein if water is the sole carrier a surfactant is also present.

2. A hair care composition according to claim 1 wherein the rigid silicone polymer is selected from the group consisting of organic substituted siloxane gums, silicone elastomers, filler reinforced polydimethyl siloxane gums, resin reinforced siloxanes and crosslinked siloxane polymers.

3. A hair care composition according to claim 2 wherein the rigid silicone polymer is a silicone elastomer and the sole volatile carrier is water.

4. A hair care composition according to claim 2 wherein the rigid silicone polymer is a filler reinforced polydimethyl siloxane gum.

5. A hair care composition according to claim 2 wherein the rigid silicone polymer is an organic substituted siloxane gum.

6. A hair care composition according to claim 2 wherein the rigid silicone polymer is a resin reinforced siloxane.

7. A hair care composition according to claim 2 wherein the volatile carrier is a cyclic silicone containing from about 3 to about 7 silicon atoms.

8. A hair care composition according to claim 4 wherein the volatile carrier is a cyclic silicone containing from about 3 to about 7 silicon atoms.

9. A hair care composition according to claim 1 in the form of a shampoo which additionally comprises from about 5% to about 50% of a synthetic surfactant or mixtures thereof.

10. A shampoo composition according to claim 9 wherein the silicone polymer comprises from about 0.05% to about 7% of the composition.

11. A shampoo composition according to claim 10 wherein the silicone polymer is a silica reinforced polydimethyl siloxane gum.

12. A shampoo composition according to claim 9 where the silicone polymer is either a polydiphenyldimethyl siloxane having a molecular weight of at least about 500,000 and wherein the diphenyl substitution is at a level of at least 3%, or a resin reinforced siloxane.

13. A shampoo composition according to claim 12 wherein the volatile solvent is a cyclic silicone containing from about 3 to about 7 silicon atoms.

14. A shampoo composition according to claim 13 wherein the synthetic surfactant is selected from the group consisting of alkyl sulfates, ethoxylated alkyl sulfates, alpha olefin sulfonates, alkyl sulfonates betaines and mixtures thereof.

15. A shampoo composition according to claim 14 wherein the surfactant is selected from the group consisting of alkyl sulfates, ethoxylated alkyl sulfates and mixtures thereof.

16. A shampoo composition according to claim 15 wherein the surfactant comprises from about 10% to about 35% of the composition.

17. A shampoo composition according to claim 14 wherein the amount of rigid silicone polymer is from about 0.75% to about 4% and the surfactant is an alkyl sulfate present at from about 12% to about 25%.

18. A shampoo composition according to claim 17 additionally comprising an ethoxylated alkyl sulfate.

19. A hair care composition according to claim 1 in the form of a conditioner which additionally comprises from about 0.1% to about 10% of a lipid vehicle material and from about 0.05% to about 5% of a cationic surfactant.

20. A conditioner composition according to claim 19, wherein the rigid silicone polymer is a silica reinforced polydimethyl siloxane gum.

21. A conditioner composition according to claim 20, wherein the volatile carrier is a cyclic silicone containing from about 3 to about 7 silicon atoms.

22. A conditioner composition according to claim 19, wherein the rigid silicone polymer is a silicone elastomer, and the volatile carrier is water.

23. A conditioner composition according to claim 19 wherein the rigid silicone polymer is a polydiphenyldimethyl siloxane gum having a molecular weight of at least about 500,000 and containing at least 3% diphenyl substitution.

24. A conditioner composition according to claim 22, wherein the rigid silicone is a resin reinforced siloxane.

25. A conditioner composition according to claim 19, wherein the lipid vehicle material contains carbon chains of from 12 to 18 carbon atoms in length.

26. A conditioner composition, according to claim 25, comprising from about 1% to about 3% of said lipid vehicle material.

27. A conditioner composition, according to claim 19, wherein said cationic surfactant vehicle material contains carbon chains of from 12 to 18 carbon atoms in length.

28. A conditioner composition, according to claim 26, comprising from about 0.2% to about 3% of said cationic surfactant vehicle material.

29. A conditioner composition, according to claim 28, wherein said cationic surfactant vehicle material is a quaternary ammonium salt.

30. A conditioner composition, according to claim 29, wherein said lipid vehicle material is selected from the group consisting of cetyl alcohol, stearyl alcohol, cetyl palmitate, glyceryl monostearate, and mixtures thereof.

31. A conditioner composition, according to claim 30, wherein said cationic surfactant vehicle material is a fatty amine.

32. A conditioner composition, according to claim 31, wherein said cationic surfactant vehicle material is di(hydrogenated tallow) dimethyl ammonium chloride.

33. A hair care composition according to claim 1 in the form of a hair tonic including their use in pump sprays.

34. A hair care composition according to claim 1 in the form of a hairspray.

35. A hair care composition according to claim 1 in the form of a mousse.

* * * * *